(12) United States Patent
Bergmann et al.

(10) Patent No.: US 9,963,737 B2
(45) Date of Patent: May 8, 2018

(54) DUAL PROBE ASSAY FOR THE DETECTION OF HETEROGENEOUS AMPLICON POPULATIONS

(71) Applicant: Roche Molecular System, Inc., Pleasanton, CA (US)

(72) Inventors: Frank Bergmann, Iffeldorf (DE); Dorothea Sizmann, Iffeldorf (DE); Heike Zitzer, Weinheim (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 65 days.

(21) Appl. No.: 14/055,469

(22) Filed: Oct. 16, 2013

(65) Prior Publication Data

US 2014/0134611 A1 May 15, 2014

Related U.S. Application Data

(60) Provisional application No. 61/715,449, filed on Oct. 18, 2012.

(30) Foreign Application Priority Data

Oct. 18, 2012 (EP) ..................................... 12188987

(51) Int. Cl.
*C12Q 1/68* (2006.01)
*C12P 19/34* (2006.01)
*C12Q 1/70* (2006.01)

(52) U.S. Cl.
CPC ......... *C12Q 1/6813* (2013.01); *C12Q 1/6816* (2013.01); *C12Q 1/707* (2013.01)

(58) Field of Classification Search
None
See application file for complete search history.

(56) References Cited

U.S. PATENT DOCUMENTS

| | | | | |
|---|---|---|---|---|
| 5,922,855 A * | 7/1999 | Liskay | ................... | C07K 14/47 536/23.5 |
| 6,284,458 B1 * | 9/2001 | Anderson | ............... | C07H 21/00 435/325 |
| 7,919,242 B2 | 4/2011 | Gupta | | |
| 8,114,595 B2 | 2/2012 | Gupta | | |
| 8,119,346 B2 | 2/2012 | Gupta | | |
| 8,163,484 B2 | 4/2012 | Gupta | | |
| 2002/0028487 A1 * | 3/2002 | La Thangue | ....... | C07K 14/4738 435/69.1 |
| 2003/0050470 A1 * | 3/2003 | An | ......................... | C07H 21/00 536/24.3 |
| 2010/0041040 A1 | 2/2010 | Babiel et al. | | |
| 2014/0127673 A1 | 5/2014 | Bergmann et al. | | |

FOREIGN PATENT DOCUMENTS

| | | | | |
|---|---|---|---|---|
| EP | 0529493 B1 | 12/1997 | | |
| EP | 1236804 A1 * | 9/2002 | ........... | C12Q 1/6851 |
| EP | 12188987 | 3/2013 | | |
| JP | 2011-120556 A2 * | 6/2011 | | |
| WO | WO 9746716 A1 * | 12/1997 | ............. | C12Q 1/707 |
| WO | WO 2007084567 A2 * | 7/2007 | ............. | C12Q 1/703 |
| WO | 2007130519 A2 | 11/2007 | | |
| WO | WO 2009087685 A2 * | 7/2009 | ........... | C12Q 1/6862 |
| WO | 2010101947 A2 | 9/2010 | | |

OTHER PUBLICATIONS

Trani et al., "A sensitive one-step real-time PCR for detection of avian influenza viruses using a MGB probe and an internal positive control," BMC Infectious Diseases, 2006, vol. 6, No. 87, pp. 1-8.*
GenBank Accession No. AF011752 [retrieved on-line Jun. 23, 2015, publicly available Aug. 1997, retrieved from: http://ncbi.nlm.nih.gov/nuccore/AF011752].*
Castillo et al., "Comparative Study on the Clinical and Virological Characteristics Among Patients With Single Occult Hepatitis B Virus (HBV), Single Occult Hepatitis C Virus (HCV), and Occult HBV and HCV Dual Infection," Journal of Medical Virology, 2007, vol. 79, pp. 236-241.*
Rolfe, Kathryn J., et al., 2005, "A real-time Taqman method for hepatitis C virus genotyping", Journal of Clinical Virology, 34:115-121.
Schroter, Matthias, et al., 2002, "Genotyping of Hepatitis C Virus Types 1, 2, 3, and 4 by a One-Step LightCycler Method Using Three Different Pairs of Hybridization Probes", Journal of Clinical Microbiology, 40 (6):2046-2050.
Yip, Shea Ping, et al., 2005, "Use of Dual TaqMan Probes to Increase the Sensitivity of 1-Step Quantitative Reverse Transcription-PCR: Application to the Detection of SARS Coronavirus", Clinical Chemistry, 51(10):1885-1888.

(Continued)

*Primary Examiner* — Young J Kim
(74) *Attorney, Agent, or Firm* — David J. Chang; Jeffery P. Bernhardt; M. Reza Savari

(57) ABSTRACT

The present invention relates to a method for amplifying and detecting a target nucleic acid in a sample, said target nucleic comprising subgroups with sequence variations and/or individual mutations, wherein an amplification of the nucleic acids in said sample is carried out. This amplification involves a polymerase, primers for generating an amplicon and at least two detectable probes specific for different sequence portions of said amplicon. Detection of the obtained amplicon is brought about by detecting hybridization of the probes mentioned above to said different sequence portions of the amplicon.

Figure 1:
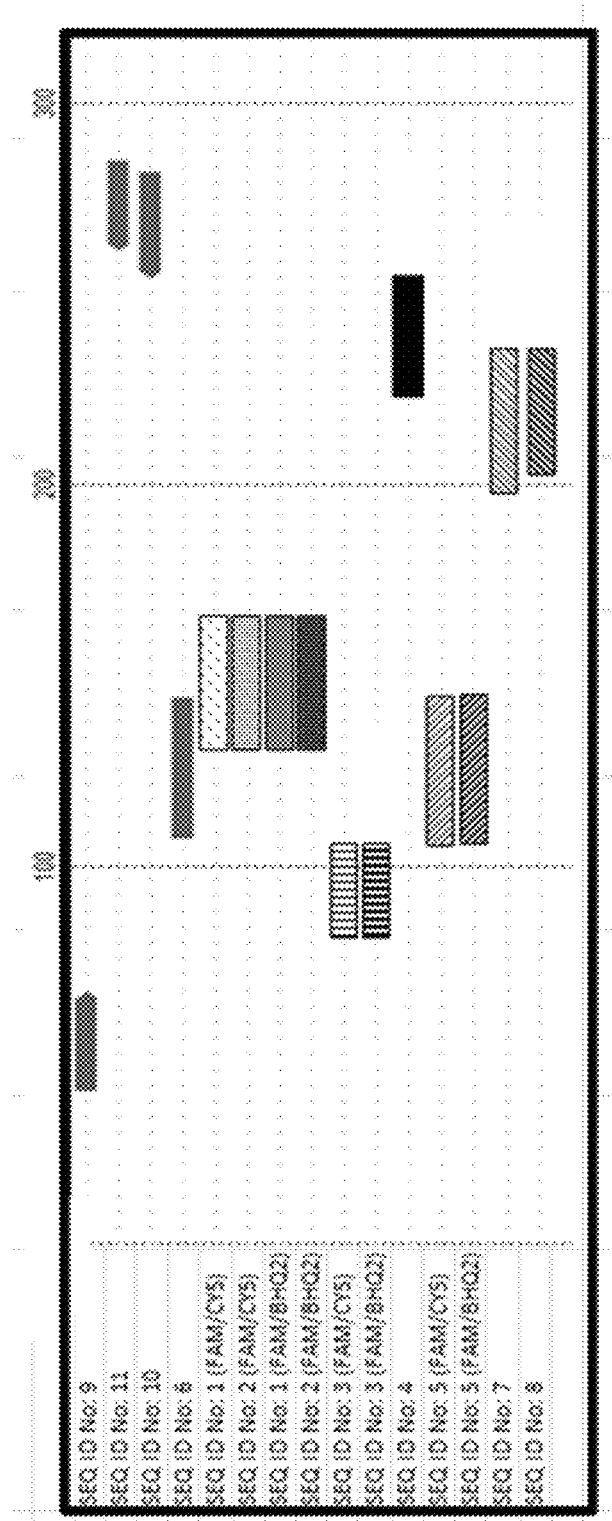

The invention further provides reaction mixtures and kits for amplifying and detecting a target nucleic acid comprising subgroups with sequence variations and/or individual mutations involving the use of at least two detectable probes specific for different sequence portions of an amplicon.

9 Claims, 9 Drawing Sheets

(56) References Cited

OTHER PUBLICATIONS

Zitzer et al., Second-Generation Cobas AmpliPrep/Cobas TaqMan HCV Quantiative Test for Viral Load Monitoring: a Novel Dual-Probe Assay Design, Feb. 2013;51(2);571-577, Epub Dec. 12, 2012.

\* cited by examiner

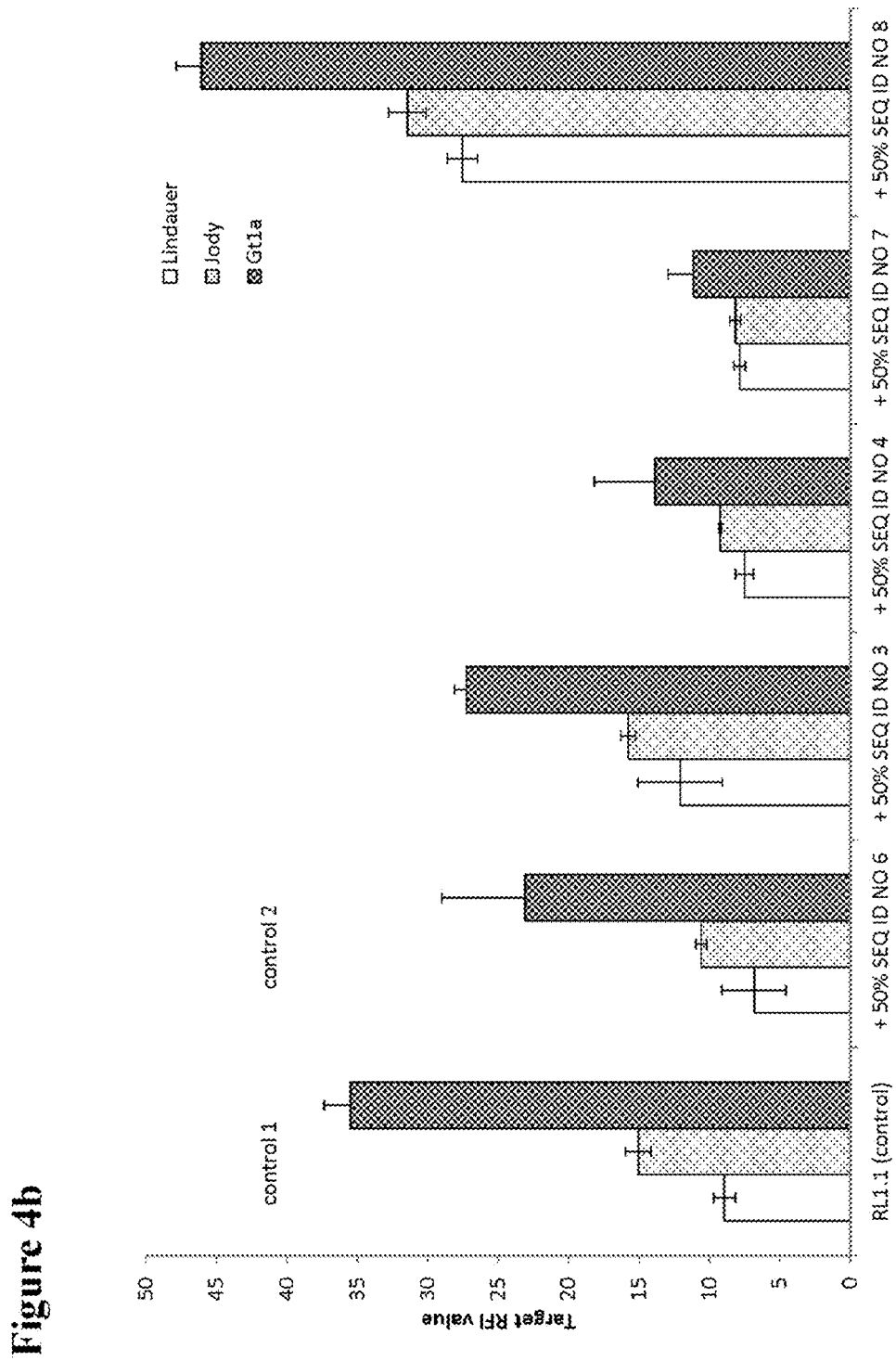

```
                         SEQUENCE LISTING

<160> NUMBER OF SEQ ID NOS: 16

<210> SEQ ID NO 1
<211> LENGTH: 35
<212> TYPE: DNA
<213> ORGANISM: Artificial Sequence
<220> FEATURE:
<223> OTHER INFORMATION: primer/probe

<400> SEQUENCE: 1
cggtgagtac accggaattg ccaggacgac cgggt                              35

<210> SEQ ID NO 2
<211> LENGTH: 35
<212> TYPE: DNA
<213> ORGANISM: Artificial Sequence
<220> FEATURE:
<223> OTHER INFORMATION: primer/probe

<400> SEQUENCE: 2
cggtgagtac accggaatcg ccgggatgac cgggt                              35

<210> SEQ ID NO 3
<211> LENGTH: 25
<212> TYPE: DNA
<213> ORGANISM: Artificial Sequence
<220> FEATURE:
<223> OTHER INFORMATION: primer/probe

<400> SEQUENCE: 3
ccgggagggg gggtcctgga ggctg                                        25

<210> SEQ ID NO 4
<211> LENGTH: 31
<212> TYPE: DNA
<213> ORGANISM: Artificial Sequence
<220> FEATURE:
<223> OTHER INFORMATION: primer/probe

<400> SEQUENCE: 4
ctagccgagt agtgttgggt cgcgaaaggc c                                 31

<210> SEQ ID NO 5
<211> LENGTH: 38
<212> TYPE: DNA
<213> ORGANISM: Artificial Sequence
<220> FEATURE:
<223> OTHER INFORMATION: primer/probe

<400> SEQUENCE: 5
cggtgtactc accggttccg aagaccacta tggctctc                          38

<210> SEQ ID NO 6
<211> LENGTH: 36
<212> TYPE: DNA
<213> ORGANISM: Artificial Sequence
<220> FEATURE:
<223> OTHER INFORMATION: primer/probe

<400> SEQUENCE: 6
cggtgtactc accgttccgc agaccactat ggctct                            36

<210> SEQ ID NO 7
```

```
<211> LENGTH: 37
<212> TYPE: DNA
<213> ORGANISM: Artificial Sequence
<220> FEATURE:
<223> OTHER INFORMATION: primer/probe

<400> SEQUENCE: 7
atttgggcgt gcccccgcaa gactgctagc cgagtag                       37

<210> SEQ ID NO 8
<211> LENGTH: 33
<212> TYPE: DNA
<213> ORGANISM: Artificial Sequence
<220> FEATURE:
<223> OTHER INFORMATION: primer/probe

<400> SEQUENCE: 8
gggcgtgccc ccgcaagact gctagccgag tag                           33

<210> SEQ ID NO 9
<211> LENGTH: 30
<212> TYPE: DNA
<213> ORGANISM: Artificial Sequence
<220> FEATURE:
<223> OTHER INFORMATION: primer/probe

<400> SEQUENCE: 9
aaaagcagaa agcgtctagc catggcgtta                               30

<210> SEQ ID NO 10
<211> LENGTH: 32
<212> TYPE: DNA
<213> ORGANISM: Artificial Sequence
<220> FEATURE:
<223> OTHER INFORMATION: primer/probe

<400> SEQUENCE: 10
aaaagcaagc accctatcag gcagtaccac aa                            32

<210> SEQ ID NO 11
<211> LENGTH: 24
<212> TYPE: DNA
<213> ORGANISM: Artificial Sequence
<220> FEATURE:
<223> OTHER INFORMATION: primer/probe

<400> SEQUENCE: 11
ctcgcaagca ccctatcagg cagt                                     24

<210> SEQ ID NO 12
<211> LENGTH: 21
<212> TYPE: DNA
<213> ORGANISM: Artificial Sequence
<220> FEATURE:
<223> OTHER INFORMATION: primer/probe

<400> SEQUENCE: 12
aaacccactc tatgtccggt c                                        21

<210> SEQ ID NO 13
<211> LENGTH: 21
<212> TYPE: DNA
<213> ORGANISM: Artificial Sequence
<220> FEATURE:
<223> OTHER INFORMATION: primer/probe

<400> SEQUENCE: 13
```

```
gtacgccgga attgccggaa a                                           21

<210> SEQ ID NO 14
<211> LENGTH: 21
<212> TYPE: DNA
<213> ORGANISM: Artificial Sequence
<220> FEATURE:
<223> OTHER INFORMATION: primer/probe

<400> SEQUENCE: 14
tggcgtctcc cacgcggctg g                                           21

<210> SEQ ID NO 15
<211> LENGTH: 21
<212> TYPE: DNA
<213> ORGANISM: Artificial Sequence
<220> FEATURE:
<223> OTHER INFORMATION: primer/probe

<400> SEQUENCE: 15
ctttccccag gacctgccgg t                                           21

<210> SEQ ID NO 16
<211> LENGTH: 30
<212> TYPE: DNA
<213> ORGANISM: Artificial Sequence
<220> FEATURE:
<223> OTHER INFORMATION: primer/probe

<400> SEQUENCE: 16
tggactcagt ccttggtcat ctcaccttct                                  30
```

DUAL PROBE ASSAY FOR THE DETECTION OF HETEROGENEOUS AMPLICON POPULATIONS

CROSS-REFERENCES TO RELATED APPLICATIONS

This application is a non-provisional of application Ser. No. 61/715,449, filed on Oct. 18, 2012, which claims the benefit of EP12188987.7 also filed on Oct. 18, 2012, the entire contents of which are hereby incorporated herein by reference in their entireties.

FIELD OF THE INVENTION

The present invention belongs to the field of in vitro diagnostics. Within this field, it concerns the amplification and detection of a target nucleic acid that may be present in a sample and particularly the amplification and detection of a target nucleic acid comprising subgroups with sequence variations and/or individual mutations, using at least two probes specific for different sequence portions of an amplicon. The invention further provides reaction mixtures and kits containing at least two probes specific for different sequence portions of an amplicon.

BACKGROUND OF THE INVENTION

In the field of molecular diagnostics, the amplification and detection of nucleic acids is of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis B (HBV) and/or C Virus (HCV) and the like. Furthermore, said amplification techniques are suitable for bacterial targets, or the analysis of oncology markers, or other targets.

Within a species, a microorganism or pathogen is often classified according to distinct groups, genotypes or subtypes based on nucleic acid sequence variation (i.e. HCV, HIV, HPV etc). In an in vitro diagnostic device, nevertheless, all groups, genotypes or subtypes should be detected and/or correctly quantified to avoid false negative diagnosis or wrong titer determination. This poses a considerable challenge for molecular diagnostic assays for e.g. detection of HIV and HCV. Furthermore constant mutation and recombination of such pathogens generate within their target nucleic acids increasing diversity which must also be covered by the molecular diagnostic assay.

The most prominent and widely-used amplification technique is the Polymerase Chain Reaction (PCR). Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification.

Automated systems for PCR-based analysis often make use of real-time detection of product amplification during the PCR process in the same reaction vessel. Key to such methods is the use of modified oligonucleotides carrying reporter groups or labels.

Detection of a microbial nucleic acid in a biological sample is crucial e.g. for recognizing an infection of an individual. Thereby, one important requirement e.g. for an assay for detection of a viral infection is inclusivity, defined such that false-negative results or underquantification of titers due to variable sequence regions on a viral genome caused by mutations have to be avoided. Mutated or partially mutated sequences within the respective genome that are possibly not amplified and/or detected in combination with the low viral load enhance the possibility of obtaining false-negative or falsely quantified results.

Several options have been published to increase the inclusivity of a molecular assay. Recently, coamplification of two different and non-overlapping target sequences within the genome of a pathogen was established (US 2010/0041040). This approach may, however, not be generally applicable if two reasonably conserved target regions cannot be identified within the genome of a pathogen or if the oligonucleotides for amplification and detection of two independent target regions interfere with each other in the master mix.

In this context, the prior art has e.g. provided methods for amplification and detection involving more than one probe based on homogeneous amplicon sequence with the aim to increase assay sensitivity (Yip et al., 2005, Clin. Chem. 51 (10)).

SHORT SUMMARY OF THE INVENTION

An aspect of the present invention is a method for amplifying and detecting a target nucleic acid in a sample, said target nucleic acid comprising subgroups with sequence variations and/or individual mutations, wherein an amplification of the nucleic acids in said sample is carried out.

This amplification involves a DNA polymerase, nucleotide monomers, primers for generating an amplicon and at least two detectable probes specific for different sequence portions of said amplicon. Detection of the obtained amplicon is brought about by detecting hybridization of the probes mentioned above to said different sequence portions of the amplicon.

The invention also relates to the use of at least two non-overlapping detectable nucleic acid probes specific for different sequence portions of the same amplicon.

Furthermore, a kit is provided for amplifying and detecting a target nucleic acid that may be present in a sample, said target nucleic acid comprising subgroups with sequence variations and/or individual mutations. The kit comprises amplification reagents comprising a DNA polymerase, nucleotide monomers, primers for generating an amplicon and at least two detectable probes specific for different sequence portions of said amplicon. In addition, reaction mixtures are provided for amplifying and detecting a target nucleic acid that may be present in a sample, said target nucleic acid comprising subgroups with sequence variations and/or individual mutations. The reaction mixtures comprises a sample or a portion of a sample, and amplification reagents comprising a DNA polymerase, nucleotide monomers, primers for generating an amplicon and at least two detectable probes specific for different sequence portions of said amplicon.

DESCRIPTION OF THE INVENTION

In a first embodiment, the present invention relates to a method for amplifying and detecting a target nucleic acid that may be present in a sample, said target nucleic acid comprising subgroups with sequence variations and/or individual mutations, said method comprising the steps of:
  a) contacting nucleic acids from said sample with amplification reagents comprising a DNA polymerase, nucleotide monomers, primers for generating an amplicon and at least two detectable probes specific for different sequence portions of said amplicon;

b) incubating said nucleic acids with said amplification reagents for a period of time and under conditions sufficient for an amplification reaction to occur;

c) detecting the presence or absence of said amplicon by detecting hybridization of said detectable probes to said different sequence portions of said amplicon, wherein the presence of said amplicon is indicative of the presence of said target nucleic acid comprising subgroups with sequence variations and/or individual mutations in said sample.

In some embodiments of the invention, one or more steps of the method described above are automated. In further embodiments, all steps are automated. Automated systems provide a number of advantages as compared to manual methods, particularly in the field of in vitro diagnostics. The skilled person is enabled to leave the system after initiating the method, thus reducing hands-on time and providing the basis for a high sample throughput in a relatively short period of time, yet at the same time increasing reproducibility of the result. This is especially, but not only, an important feature in situations with a high number of clinical samples to be screened as quickly as possible, such as e.g. in blood banks.

In the context of the present invention, the term "amplifying" or "amplification" generally refers to the production of a plurality of nucleic acid molecules from a target nucleic acid wherein primers hybridize to specific sites on the target nucleic acid molecules in order to provide an initiation site for extension by a polymerase, e.g., a DNA polymerase. Amplification can be carried out by any method generally known in the art, such as but not limited to: standard PCR, realtime PCR, long PCR, hot start PCR, qPCR, Reverse Transcription PCR and Isothermal Amplification.

It can be favorable to monitor the amplification reaction in real time, i.e. to detect the target nucleic acids and/or their amplificates during the amplification itself.

The term "detecting" or "detection" as used herein relates to a test aimed at assessing the presence or absence of a target nucleic acid in a sample.

A "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined. The target nucleic acid may be a genomic sequence, e.g. part of a specific gene, or RNA. In other embodiments, the target nucleic acid may be viral or bacterial. Target nucleic acids can comprise subgroups with distinct sequence variations or distinct individual mutations in the amplicon region. This is especially the case for nucleic acids of pathogens like viruses which show significant genetic variation due to high mutation or recombination rates and lacking repair mechanisms.

The term "amplicon" refers to a polynucleotide molecule (or collectively the plurality of molecules) produced following the amplification of a particular target nucleic acid. The amplification method used to generate the amplicon can be any suitable method, for example, a PCR. An amplicon is typically, but not exclusively, a DNA amplicon. An amplicon can be single-stranded or double-stranded, or a mixture thereof in any concentration ratio. In an embodiment of the invention, the amplicon consists of subpopulations with heterogeneous sequences between the primer sequences.

The method set out above is in some embodiments based on Fluorescence Resonance Energy Transfer (FRET) between a donor fluorescent moiety and an acceptor fluorescent moiety. In these embodiments, the detectable probes specific for different sequence portions of the amplicon are FRET probes. A representative donor fluorescent moiety is fluorescein, and representative corresponding acceptor fluorescent moieties include LC-Red 640, LC-Red 705, CY5, and CY5.5. Typically, detection includes exciting the sample at a wavelength absorbed by the donor fluorescent moiety and visualizing and/or measuring the wavelength emitted by the corresponding acceptor fluorescent moiety. In the method described above, detection is in some embodiments followed by quantitating the FRET. In the context of the invention, the teens "FRET" or "fluorescent resonance energy transfer" or "Foerster resonance energy transfer" can be used interchangeably and refer to a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used donors are e.g. fluoresceins, coumarins, cyanines and rhodamines. Commonly used quenchers are DABCYL and TAMRA. Commonly used dark quenchers include BlackHole Quenchers™ (BHQ), (Biosearch Technologies, Inc., Novato, Cal.), Iowa Black™ (Integrated DNA Tech., Inc., Coralville, Iowa), and BlackBerry™ Quencher 650 (BBQ-650) (Berry & Assoc., Dexter, Mich.).

A common format of FRET technology utilizes two hybridization probes forming a HybProbe pair. Each probe can be labeled with a different fluorescent moiety. The probes are generally designed to hybridize in close proximity to each other in a target DNA molecule (e.g., an amplification product). A donor fluorescent moiety like e.g. fluorescein is excited at 470 nm by the light source e.g. of a LIGHTCYCLER® instrument. During FRET, the fluorescein transfers its energy to an acceptor fluorescent moiety such as e.g. LIGHTCYCLER®-Red 640 (LC®-Red 640) or LIGHTCYCLER®-Red 705 (LC®-Red 705). The acceptor fluorescent moiety then emits light of a longer wavelength, which is detected by the optical detection system of the LIGHTCYCLER® instrument. Efficient FRET can only take place when the fluorescent moieties are in direct local proximity (usually about 1 to 5 nucleotides distance) and when the emission spectrum of the donor fluorescent moiety overlaps with the absorption spectrum of the acceptor fluorescent moiety. The intensity of the emitted signal can be correlated with the number of original target nucleic acid molecules. In the context of the present invention, as also appreciated by the person skilled in the art, a HybProbe pair is to be understood as a functional unity and thus a single probe, since the two members of such a pair have to be used together.

Hence, the distinct probes of a HybProbe pair do not form "detectable probes specific for different sequence portions" of an amplicon even though they do not overlap when binding to the amplicon. However, e.g. two or more HybProbe pairs are "detectable probes specific for different sequence portions of said amplicon" in the sense of the invention, since as described above a HybProbe pair is to be understood as a single probe.

In an embodiment of the method described above, the detectable probes specific for different sequence portions of said amplicon are HybProbe pairs.

This embodiment confers several advantages. For instance, since the probes in this detection format are not degraded, melting curve analyses may be performed on each of the HybProbe pairs by monitoring the temperature dependence of their hybridization. As the skilled person knows, melting curve analysis is suitable for verification of results or even provision of more detailed information e.g. on the identity of a target nucleic acid than monitoring hybridization at a single temperature may yield.

Detection of amplicon formation on Cobas® TaqMan® systems utilizes a single-stranded hybridization probe (also termed "5'-nuclease probe"). The term "5'-nuclease probe" refers to an oligonucleotide that comprises at least one light emitting labeling moiety and that is used in a 5'-nuclease reaction to effect target nucleic acid detection. In some embodiments, for example, a 5'-nuclease probe includes only a single light emitting moiety (e.g., a fluorescent dye, etc.). In certain embodiments, 5'-nuclease probes include regions of self-complementarity such that the probes are capable of forming hairpin structures under selected conditions. To further illustrate, in some embodiments a 5'-nuclease probe comprises at least two labeling moieties and emits radiation of increased intensity after one of the two labels is cleaved or otherwise separated from the oligonucleotide. In certain embodiments, a 5'-nuclease probe is labeled with two different fluorescent dyes, e.g., a 5' terminus reporter dye and a 3' terminus quencher dye or moiety. In some embodiments, 5'-nuclease probes are labeled at one or more positions other than, or in addition to, terminal positions. When the probe is intact, energy transfer typically occurs between the two fluorophores such that fluorescent emission from the reporter dye is quenched at least in part. During an extension step of a polymerase chain reaction, for example, a 5'-nuclease probe bound to a template nucleic acid is cleaved by the 5' to 3' nuclease activity of, e.g., a Taq polymerase or another polymerase having this activity like e.g. the Z05 polymerase, such that the fluorescent emission of the reporter dye is no longer quenched. Exemplary 5'-nuclease probes are described in, e.g., U.S. Pat. No. 5,210,015. In some embodiments, a 5' nuclease probe may be labeled with two or more different reporter dyes and a 3' terminus quencher dye or moiety. Typical fluorescent dyes used in this format are for example, among others, FAM, HEX, CY5, JA270, Cyan500 and CY5.5.

In an embodiment of the method described above, the detectable probes specific for different sequence portions of said amplicon are 5'-nuclease probes.

The detectable probes can hybridize to the same or to different strands of a double-stranded amplicon.

In some embodiments of the method described above, at least two detectable probes hybridize to different strands of said amplicon.

In this case, the skilled person is provided with increased flexibility with regard to selecting the primer and probe sequences and thus binding sites on the respective amplicon. For instance, in the case of secondary structure formation due to a specific sequence within an oligonucleotide, it can be important to be able to switch to a different sequence and thus to a different binding site on said amplicon. Further, if the detectable probes bind to different strands, such as a first probe to the sense strand and a second probe to the antisense strand of a double-stranded amplicon, the risk of those probes interfering with each other at their respective binding sites is reduced.

In further embodiments of the method described above, at least two detectable probes hybridize to the same strand of said amplicon.

In that latter embodiment, it is possible to hybridize multiple detectable probes specific for different sequence portions of the amplicon in close vicinity to each other. This is surprising due to the circumstance that the respective exonuclease requires some space to bind and cleave the 5'-nuclease probes. Yet, the inventors have shown that even such probes can be hybridized to an amplicon at only few bases of distance between one another. This enables the skilled person to use more than one detectable probe specific for distinct sequence portions each to amplicons of relatively short length. According to the method described above, even short stretches of target nucleic acids can serve as suitable targets for multiple probes, thus conferring the benefits described supra, such as e.g. signal enhancement and increased tolerance against genetic variations like e.g. point mutations.

Thus, in an embodiment of the method described above, the detectable probes specific for different sequence portions of said amplicon hybridize to the amplicon with no more than 100 bases distance to each other, in some embodiments from 1, 5, 10, 20, 30, 40 or 50 bases, to 60, 70, 80, 90, or 100 bases distance to each other. In some embodiments, the distance is from 40 to 80, or from 50 to 70, or from 55 to 60 bases, or it is 58 bases. In this context, "distance" means the number of bases of the amplicon lying between those bases of the amplicon to which the detectable probes hybridize in case they hybridize to the same strand. If they hybridize to different strands, the distance is calculated accordingly, wherein each base of one strand of a double-stranded amplicon has a corresponding base on the other strand with which it forms a base pair.

In some embodiments, detection is performed after each cycling step of a cycle-based amplification technique such as PCR. In some embodiments, detection is performed in real time. By using commercially available real-time PCR instrumentation (e.g., LightCycler® or TaqMan®), PCR amplification and detection of the amplification product can be combined in a single closed cuvette with considerably reduced cycling time. Since detection occurs concurrently with amplification, real-time PCR methods obviate the need for manipulation of the amplification product, and diminish the risk of cross-contamination between amplification products. In both detection formats described above, the intensity of the emitted signal can principally be correlated with the number of original target nucleic acid molecules.

A "sample" is any material that can be subjected to a diagnostic assay and generally refers to the medium possibly containing the target nucleic acid. The "sample" is in some embodiments derived from a biological source. The sample can be e.g. a clinical sample. In some embodiments, said sample is derived from a human and is a body liquid. In some embodiments of the invention, the sample is human whole blood or serum, blood plasma, urine, sputum, sweat, genital or buccal or nasal swabs, pipettable stool, solubilized tissue samples, or spinal fluid or the like. A sample can be pipetted or converted to a pipettable form, such that the term "sample" comprises homogeneous or homogenized liquids, but also emulsions, suspensions and the like. A sample may also e.g. be an originally solid sample (i.e. tissue sample) which is subjected to a solubilization treatment for extraction and purification of nucleic acids.

A "polymerase" as used herein is an enzyme capable of synthesizing nucleic acids from smaller elements such as nucleotides. In some embodiments, the nucleic acid polymerase is a DNA polymerase. In some embodiments, the polymerase is a thermostable polymerase. The term "thermostable polymerase" refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. For amplification purposes, said nucleotides are present in monomeric form, therefore they are also referred to as "nucleotide monomers" in the context of the present invention. Often, such nucleotide monomers used by polymerases such as e.g. thermostable DNA polymerases are e.g. nucleoside triphosphohates, or nucleoside tetraphosphates, or the like. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species Sps17, *Thermus* species Z05, *Thermus caldophilus, Bacillus caldotenax, Thermotoga neopolitana*, and *Thermosipho africanus*.

The term "primer" is used herein as known to the expert skilled in the art and refers to oligomeric compounds, primarily to oligonucleotides, but also to modified oligonucleotides that are able to prime DNA synthesis by a template-dependent DNA polymerase, i.e. the 3'-end of the primer provides a free 3'-OH group whereto further nucleotides may be attached by a template-dependent DNA polymerase establishing 3'- to 5'-phosphodiester linkage whereby deoxynucleoside triphosphates are used and whereby pyrophosphate is released.

A "probe" or "detectable probe" also denotes a natural or modified oligonucleotide. As known in the art, a probe serves the purpose of detecting an analyte or amplificate. In the context of the invention, probes can e.g. be used to detect the amplificates of the target nucleic acid and/or a control nucleic acid. For the purpose of detectability, probes typically carry labels.

In some embodiments of the method the at least two detectable probes specific for different sequence portions of said amplicon carry the same type of label and thus the signal originating from the individual probe cannot be distinguished. In other embodiments, they carry different labels emitting signals of different wavelengths such that the signals from the at least two probes can be distinguished with the appropriate instrumentation.

"Labels", often referred to as "reporter groups", are generally groups that make a nucleic acid, in particular oligonucleotides or modified oligonucleotides, as well as any nucleic acids bound thereto distinguishable from the remainder of the sample. Useful labels in the context of the invention are e.g. fluorescent labels, which may be fluorescent dyes such as for instance a fluorescein dye, a rhodamine dye, a cyanine dye, or a coumarin dye. Useful fluorescent dyes in the context of the invention are e.g. FAM, HEX, JA270, CAL635, Coumarin343, Quasar705, Cyan500, CY5.5, LC-Red 640, LC-Red 705, TAMRA, or CY5.

In the context of the invention, any primer and/or probe may be chemically modified, i.e. the primer and/or the probe comprise a modified nucleotide or a non-nucleotide compound. The probe or the primer is then a modified oligonucleotide.

As known by the person skilled in the art, the term "specific" in the context of primers and probes implies that a primer or probe "specific" for a distinct nucleic acid binds to said nucleic acid under stringent conditions. In some embodiments the probes used in the context of the invention are at least 80% identical to the different sequence portions of the amplicon. In another embodiment, the probe sequences comprise at least 12 contiguous nucleotides of a sequence selected from the group consisting of SEQ ID NOs: 1 to 8 or the corresponding complementary nucleic acid sequences thereof, and the primers comprise at least 12 contiguous nucleotides of SEQ ID NOs: 9 to 15. In some embodiments, the selected probe and/or primer sequences consist of 12 to 60 nucleotides, or of 20 to 60 nucleotides, or of the exact sequences selected from said SEQ ID NOs:1-15 or their complementary nucleic acid sequences. The skilled person understands that, in the sense of the invention, a probe pair forming a functional entity such as e.g. a Hybprobe pair used in the LightCycler® instrument is not "at least two detectable probes specific for different sequence portions of said amplicon". The two Hybprobes of a pair are regarded as a unit and can only be detected together, while each of the at least two probes in the context of the invention is detectable alone.

Furthermore, in the context of the invention the term "overlap" means that two or more oligonucleotides, in particular the at least two detectable probes mentioned supra, comprise identical (when bound to the same strand) or complementary (when bound to different strands) sequence stretches. The probes used in the method described above in some embodiments do not overlap and thus do not compete in binding to a specific site on the amplicon. When bound, said two or more probes are hybridized to different sequence stretches of said amplicon. The detectable probes used in the context of the invention are advantageous as compared to overlapping probes.

The term "hybridize" or "hybridization" generally refers to the base-pairing between different nucleic acid molecules consistent with their nucleotide sequences. The terms "hybridize" and "anneal" can be used interchangeably.

Directing two or more probes to different sequence portions of the same amplicon, as performed in the method described supra, leads to a significantly reduced risk of obtaining false-negative results in qualitative assays. Moreover, in quantitative assays, the risk to underquantitate titers e.g. of a virus is reduced. A variety of different genotypes, subtypes and mutants within a given organism can be readily detected and quantified using a minimum number of oligonucleotides as a result of the increased inclusivity and robustness of the assay. In that respect, it may be the case that a certain genotype, subtype or mutant is not hybridized to by all of the at least two detectable probes. For instance, in the case of two probes, one might not bind to the target amplicon because of the specific sequence variant of the latter, whereas the other probe specific for a different sequence portion of said amplicon is still capable of hybridizing to its respective target sequence. This way, detection of the amplicon would still be possible. In embodiments where the different probes carry different labels, it may also be possible to determine which of the probes hybridized and which ones did not.

The life cycle of tests based on the method described above is prolonged, since it is able to deal even with new variants generated by microorganisms such as e.g. viruses through selective pressure for example as a consequence of new antiretroviral drugs. In view of the high degree of mutations within viral genomes, in an embodiment of the method described above said target nucleic acid is a viral nucleic acid.

Overall inclusivity of qualitative assays is significantly increased, and the variability of titer determinations in quantitative assays is minimized by applying the method described above.

As known by the skilled person, a measure for the inclusivity is the detection of viral subgroups and isolates carrying mutations with equivalent sensitivity as the standard isolates not significantly deviating from the consensus sequence. Sensitivity of an assay is the LOD (Limit Of Detection), referring to the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is a copy of the respective nucleic acid. IU/ml stands for "International units/ml", referring to the WHO standard. The WHO standards are generally built from a standard isolate with a genome close to the consensus sequence.

A widely used method for calculating an LOD is the "Probit Analysis" which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The Probit Analysis can be applied at distinct "hitrates". As known in the art, a "hitrate" is commonly expressed in percent [%] and indicates the percentage of positive results at a specific concentration of an analyte. Thus for example, an LOD can be determined at 95% hitrate, which means that the LOD is calculated for a setting in which 95% of the valid results for a true positive sample are determined as positive.

The method described above is particularly advantageous in assays for detecting Hepatitis C-Virus (HCV). Thus, in an embodiment of the method described supra; the target nucleic acid is a nucleic acid of HCV.

The expression "hepatitis C virus type" refers to the categorization of a hepatitis C virus based on its genomic organization (e.g., phylogenetic analysis). The categorization of an HCV isolate into a particular type category reflects its genomic relatedness to other HCV isolates and its relatively lesser relatedness to other HCV isolates. The HCV typing nomenclature used herein is consistent with the widely adopted nomenclature revised and proposed by Simmonds et al (2005) "Consensus Proposals for a Unified System of Nomenclature of Hepatitis C Virus Genotypes", Hepatology 42, No. 4:962-973. The system of Simmonds et al (2005) places the known HCV isolates into one of six (6) HCV genotypes, namely genotypes 1 through 6. Each genotype is further subdivided into groupings termed subtypes that reflect relatedness among strains of the same genotype.

An HCV subtype is written by a lowercase Roman letter following the genotype, e.g., subtype 1a, subtype 1c, subtype 6a, etc. Genetic variants found within an individual isolate are termed quasi species. Approximately 100 HCV subtypes encompassing all six genotypes are known worldwide. The number of subtypes is not static, i.e. as more HCV isolates are studied and sequenced, it is likely that additional subtypes (and possibly genotypes) may be recognized.

Since HCV is an RNA virus, the person skilled in the art usually reversely transcribes the viral RNA into DNA prior to the actual amplification. In such a case, the amplification reagents comprise a reverse transcriptase or a polymerase with reverse transcriptase activity.

A primer suitable for annealing to an RNA template may also be suitable for amplification by PCR. For PCR, a second primer, complementary to the reverse transcribed cDNA strand, provides an initiation site for the synthesis of an extension product.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "one-step real-time PCR", in this context, may refer to a reaction without reverse transcription step if target nucleic acid is DNA or a reaction including a reverse transcription step if target nucleic acid is RNA. By "one-step real-time PCR" it is meant that following the reverse transcription (RT) step, there is no need to open the reaction vessel or otherwise adjust reaction components prior to the amplification step. In a non-one-step real-time PCR reaction, following reverse transcription and prior to amplification one or more of the reaction components such as the amplification reagents are e.g. adjusted, added, or diluted, for which the reaction vessel has to be opened, or at least its contents have to be manipulated. Both one-step real-time PCR and non-one-step real-time PCR embodiments are comprised by the scope of the invention.

In an embodiment of the invention carryover contamination of amplification products such as amplicons and high molecular weight products (polymerized amplicon) originating from earlier PCR reactions are prevented. A popular and effective way of preventing carryover contamination involves the use of uracil-DNA glycosylases or uracil-N-glycosylases, abbreviated as "UDG" or "UNG" (EC 3.2.2.3). These enzymes comprising uracil-DNA glycosylase activity recognize uracil present in single-stranded or double-stranded DNA and cleave the N-glycosidic bond between the uracil base and the deoxyribose leaving an abasic site, see e.g. U.S. Pat. No. 6,713,294.

As shown by the examples herein, a particularly good performance in detecting a nucleic acid of HCV is achieved when employing probes comprising or consisting of at least two sequences selected from the group consisting of SEQ ID NOs:1 to 8 or the respective complements thereof. Hence, an aspect of the invention is a method for amplifying and detecting a target nucleic acid of HCV that may be present in a sample, said method comprising the steps of:

a) contacting nucleic acids from said sample with amplification reagents comprising a polymerase, nucleotide monomers, primers for generating an amplicon and at least two detectable probes specific for different sequence portions of said amplicon, wherein said at least two detectable probes comprise at least two sequences selected from the group consisting of SEQ ID NOs:1 to 8 or the respective complements thereof;

b) incubating said nucleic acids with said amplification reagents for a period of time and under conditions sufficient for an amplification reaction to occur;

c) detecting the presence or absence of said amplicon by detecting hybridization of said detectable probes to said different sequence portions of said amplicon;

wherein the presence of said amplicon is indicative of the presence of HCV in said sample.

In a further embodiment of the method described above, said at least two detectable probes comprise SEQ ID NOs:6 and 8, in yet another embodiment the amplification reagents contain no further HCV-specific probes apart from SEQ ID NOs:6 and 8.

In an embodiment of the invention, the primers in the method mentioned above comprise at least one sequence selected from the group consisting of SEQ ID NOs:9 to 15. Said primers are particularly useful for creating an amplicon detectable with the probes mentioned above. In another embodiment, the primers in the method mentioned above consist of SEQ ID NOs: 9, 10, and 11.

Also an aspect of the invention is the method described above, wherein said primers comprise more than one forward and/or reverse primer. Such an arrangement can be especially useful when these primers lead to variable, overlapping amplicons detectable by the probes mentioned above. In the case of more than one forward and/or reverse primer, the respective forward and/or reverse primers are in some embodiments staggered, i.e. they overlap with respect to the template sequence they hybridize to. Such a staggered constellation further contributes to an increased coverage of genetic variants such as HCV genotypes and/or subtypes.

The combination of the primers and probes mentioned above in the method set out supra is particularly useful for detecting a considerable variety of HCV genotypes. In an embodiment, the method described above is a method for simultaneously detecting Genotypes 1, 2, 3, 4, 5, and 6 of HCV that may be present in a sample. In a further embodiment, the method described above is a method for detecting Genotypes 1, 2, 3, and 5 (Subset 1) with a fully matching first probe and Genotypes 1, 2, 4, and 6 (Subset 2) with a fully matching second probe. In a further embodiment, the method is a method for detecting Subtypes 1a, 1b, 2a, 2b and in some embodiments further Subtypes. In yet another embodiment, the method described above is a method for simultaneously detecting Genotypes 1, 2, 3, 4, 5, and 6 as well as Subtypes 1a, 1b, 2a, 2b and in some embodiments further Subtypes of HCV that may be present in a sample.

A further aspect of the invention is the method described above, further comprising prior to step a) the steps of:

i) combining together a solid support and said sample for a period of time and under conditions sufficient to permit nucleic acids comprising said target nucleic acid to be immobilized on said solid support;

ii) isolating said solid support from the other material present in the sample in a separation station;

iii) purifying the nucleic acids in the separation station by separating the sample from the solid support and washing the solid support one or more times with a wash buffer.

In the context of the invention, the term "solid support" as used herein relates to any type of solid support to which the analyte is capable of binding, either directly and non-specifically by adsorption, or indirectly and specifically.

Indirect binding may be binding of an analyte to an antibody immobilized on the solid support, or binding of a tag to a tag binding compound, e.g. binding of 6×His tags to Ni-chelate. When the analyte is a nucleic acid, such indirect binding may be by binding to a capture nucleic acid probe which is homologous to a target sequence of the nucleic acid of interest. Thus, using capture probes attached on a solid support, a target analyte, or a target nucleic acid, can be separated from non-target material, or non-target nucleic acid. Such a capture probe is immobilized on the solid support. Solid support material may be a polymer, or a composition of polymers. Other types of solid support material include magnetic silica particles, metal particles, magnetic glass particles, glass fibers, glass fiber filters, filter paper etc., while the solid support material is not limited to these materials.

"Immobilize", in the context of the invention, means to capture objects such as nucleic acids in a reversible or irreversible manner. Particularly, "immobilized on the solid support material", means that the object or objects are associated with the solid support material for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture probes, wherein nucleic acids are bound to essentially complementary nucleic acids attached to a solid support by base-pairing. In the latter case, such specific immobilization leads to the predominant binding of target nucleic acids.

A "separation station" is a device or a component of an analytical system allowing for the isolation of the solid support from the other material present in the sample. Such a separation station can e.g. comprise, while it is not limited to these components, a centrifuge, a rack with filter tubes, a magnet, or other suitable components. In some embodiments, the separation station comprises one or more magnets. In certain embodiments, one or more magnets are used for the separation of magnetic particles, such as e.g. magnetic glass particles, as a solid support. If, for example, the sample and the solid support material are combined together in the wells of a multiwell plate, then one or more magnets comprised by the separation station can e.g. be contacted with the sample itself by introducing the magnets into the wells, or said one or more magnets can be brought close to the outer walls of the wells in order to attract the magnetic particles and subsequently separate them from the surrounding liquid.

In the sense of the invention, "purification", "isolation" or "extraction" of nucleic acids relate to the following: Before nucleic acids may be analyzed in a diagnostic assay e.g. by amplification, they typically have to be purified, isolated or extracted from biological samples containing complex mixtures of different components. For the first steps, processes may be used which allow the enrichment of the nucleic acids.

A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components. The wash buffer may, for example, contain ethanol and/or chaotropic agents in a buffered solution or solutions with an acidic pH without ethanol and/or chaotropic agents as described above. Often the washing solution or other solutions are provided as stock solutions which have to be diluted before use.

Summarizing, by applying the steps i) to iii) of the method described above, the nucleic acids including the target nucleic acid that may be present in the sample are separated from the remainder of the sample, such that the risk of inhibition of the subsequent steps by any potentially interfering substances in said sample is reduced.

For downstream analysis, the nucleic acids may subsequently be eluted from the solid support e.g. by means of an appropriate elution buffer. Such an elution buffer may e.g. be distilled or deionized water or aqueous salt solutions, such as e.g. Tris buffers like Tris HCl, or HEPES, or other suitable buffers known to the skilled artisan.

In some embodiments, the solid support is present in the amplification reaction mixture during amplification and in some embodiments also detection.

In some embodiments of the method described supra, a control nucleic acid is added to the sample and/or the purified nucleic acids.

Said control nucleic acid is in some embodiments a qualitative control nucleic acid, and in other embodiments a quantitative control nucleic acid, or both.

Qualitative detection of a nucleic acid in a sample is crucial e.g. for recognizing an infection of an individual. Thereby, one important requirement for an assay for detection e.g. of a viral infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the respective target nucleic acid, the qualitative internal control reaction has to perform reactive within given settings, i.e. the qualitative internal control must be detected, or otherwise the test itself is considered to be inoperative. However, in a qualitative setup, said qualitative internal control does not necessarily have to be detected in case of a positive result. For qualitative tests, it is especially important that the sensitivity of the reaction is guaranteed and therefore strictly controlled. In consequence, the concentration of the qualitative internal control must be relatively low so that even in a situation e.g. of slight inhibition the qualitative internal control is not detected and therefore the test is invalidated.

Thus, in an embodiment of the method described above, the presence of an amplification product of said control nucleic acid is indicative of an amplification occurring in the reaction mixture even in the absence of amplification products for said target nucleic acid.

On the other hand and in addition to mere detection of the presence or absence of a nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success.

Hence, an aspect of the invention is the method described above, further comprising the step of determining the quantity of the target nucleic acid comprising subgroups with sequence variations and/or individual mutations after and/or during step c).

For instance, HCV RNA viral load tests are used as an aid in the management of chronic hepatitis C patients by evaluating treatment response and making clinical decisions e.g. regarding treatment duration. The primary goal of a therapy for chronic hepatitis C is to eradicate the HCV by achieving a sustained virologic response, e.g. in the case of treatment with medicaments like peginterferon alpha-2, alone or in combination with further drugs such as ribavirin and/or boceprevir or telaprevir. The method described above provides a viral load assay that reliably detects and quantifies HCV RNA leading to improved on-treatment monitoring.

For a quantitative assay, it is necessary to introduce a quantitative standard nucleic acid serving as a reference for determining the absolute quantity of a target nucleic acid. Thus, a quantitative internal control nucleic acid is added to the detection mix. Said control is particularly important for quantification of the test result but also for confirming the validity of a test result: The quantitative internal control nucleic acid must be detected in the case of a negative and a positive result with regard to the respective target nucleic acid. The quantitative internal control reaction has to perform reactive within given settings or otherwise the test itself is considered to be inoperative. Quantitation can be effectuated either by referencing to an external calibration or by implementing an internal quantitative standard.

An example of how to perform calculation of quantitative results for signals generated on a Cobas® TaqMan® system based on an internal control nucleic acid serving as a quantitative standard nucleic acid is described in the following: A titer is calculated from input data of instrument-corrected fluorescence values from an entire PCR run. A set of samples containing a target nucleic acid and an internal control nucleic acid serving as a quantitative standard nucleic acid undergo PCR on a thermocycler using a specified temperature profile. At selected temperatures and times during the PCR profile samples are illuminated by filtered light and the filtered fluorescence data are collected for each sample for the target nucleic acid and the internal control nucleic acid. After a PCR run is complete, the fluorescence readings are processed to yield one set of dye concentration data for the internal control nucleic acid and one set of dye concentration data for the target nucleic acid. Each set of dye concentration data is processed in the same manner. After several plausibility checks, the elbow values (CT) are calculated for the internal control nucleic acid and the target nucleic acid. The elbow value is defined as the point where the fluorescence of the target nucleic acid or the internal control nucleic acid crosses a predefined threshold (fluorescence concentration). Titer determination is based on the assumptions that the target nucleic acid and the internal control nucleic acid are amplified with the same efficiency and that at the calculated elbow value equal amounts of amplicon copies of target nucleic acid and internal control nucleic acid are amplified and detected. Therefore, the (ctQS−ctTarget) is linear to log (target conc/QS conc). In this context, QS denotes the internal control nucleic acid serving as a quantitative standard nucleic acid. The titer T can then be calculated for instance by using a polynomial calibration formula as in the following equation:

$$\text{conc}_{T\ arg\ et} = \text{conc}_{QS} \cdot 10^{(a \cdot (CtQS-ctT\ arg\ et)^2 + b \cdot (ctQS-ctT\ arg\ et)+c)}$$

The polynomial constants and the concentration of the quantitative standard nucleic acid are known, such that the only variable in the equation is the difference (ctQS−ctTarget).

As known by the person skilled in the art, important values for characterizing a good quantitative assay are e.g. the assay's linearity or linear range (determined by quantitation of a dilution series of the target material with subsequent linear regression of the resulting curve), accuracy (correlation between nominal and experimentally determined/assigned values), inclusivity (equivalent and accurate quantification of genotypes/subtypes/mutants/isolates) and precision (standard deviation of the $\log_{10}$ transformed concentration result determined by variance component analysis using data generated from linearity studies).

For both quantitative and qualitative tests, also properties like analytical sensitivity (described above in the context of LOD) or specificity (avoidance of false-positive results due to unspecific detection) are significant parameters. It is shown in the examples herein that the method described above displays improved properties with regard to inclusivity as discussed above.

In line with the advantages of the method as discussed above, another aspect of the invention is the use of at least two detectable nucleic acid probes for amplifying and detecting a target nucleic acid that may be present in a sample, said target nucleic acid comprising subgroups with sequence variations and/or individual mutations, wherein said detectable nucleic acid probes are specific for different sequence portions of the same amplicon.

In some embodiments of the use described above, said detectable probes do not overlap.

In further embodiments, the use described above is a use of at least two detectable nucleic acid probes for amplifying and detecting a target nucleic acid of HCV that may be present in a sample, wherein said detectable nucleic acid probes are specific for different sequence portions of the same amplicon, and wherein said detectable probes comprise at least two sequences selected from the group consisting of SEQ ID NOs:1 to 8 or the respective complements thereof.

In a further embodiment of the use described above, said at least two detectable probes comprise SEQ ID NOs:6 and 8, in yet another embodiment the kit contains no further HCV-specific probes apart from SEQ ID NOs:6 and 8.

Further provided by the invention is a kit for amplifying and detecting a target nucleic acid that may be present in a sample, said target nucleic acid comprising subgroups with sequence variations and/or individual mutations, said kit comprising amplification reagents comprising a polymerase, nucleotide monomers, primers for generating an amplicon and at least two detectable probes specific for different sequence portions of said amplicon.

In some embodiments of the kit described above, said detectable probes do not overlap.

In an embodiment, the kit mentioned supra is a kit for amplifying and detecting a target nucleic acid of HCV that may be present in a sample, said kit comprising amplification reagents comprising a polymerase, nucleotide monomers, primers for generating an amplicon and at least two detectable probes specific for different sequence portions of said amplicon, wherein said detectable probes comprise at least two sequences selected from the group consisting of SEQ ID NOs:1 to 8 or the respective complements thereof.

In a further embodiment of the kit described above, said at least two detectable probes comprise SEQ ID NOs:6 and 8, in yet another embodiment the kit contains no further HCV-specific probes apart from SEQ ID NOs:6 and 8.

The detectable probes of the kit described above can hybridize to the same or to different strands of a double-stranded amplicon.

In some embodiments of the method described above, at least two detectable probes hybridize to different strands of said amplicon. In further embodiments, at least two detectable probes hybridize to the same strand of said amplicon.

In another embodiment of the kit described above, the detectable probes specific for different sequence portions of said amplicon hybridize to the amplicon with no more than 100 bases distance to each other, in some embodiments from 1, 5, 10, 20, 30, 40 or 50 bases, to 60, 70, 80, 90, or 100 bases distance to each other. In some embodiments, the distance is from 40 to 80, or from 50 to 70, or from 55 to 60 bases, or it is 58 bases. In this context, "distance" means the number of bases of the amplicon lying between those bases of the amplicon to which the detectable probes hybridize in case they hybridize to the same strand. If they hybridize to different strands, the distance is calculated accordingly, wherein each base of one strand of a double-stranded amplicon has a corresponding base on the other strand with which it forms a base pair.

In an embodiment of the invention, the primers of the kit described above comprise more than one forward and/or reverse primer.

In an embodiment of the invention, the primers in the kit mentioned above comprise at least one element selected from the group consisting of SEQ ID NOs: 9 to 15. Said primers are particularly useful for creating an amplicon detectable with the probes mentioned above. In another embodiment, the primers in the kit mentioned above are SEQ ID NOs: 9, 10 and 11.

The advantages for said use and said kit are analogous to the ones described further supra in the context of the method according to the invention.

SHORT DESCRIPTION OF THE FIGURES

FIG. 1: Overview of probes tested.

Figure 2:
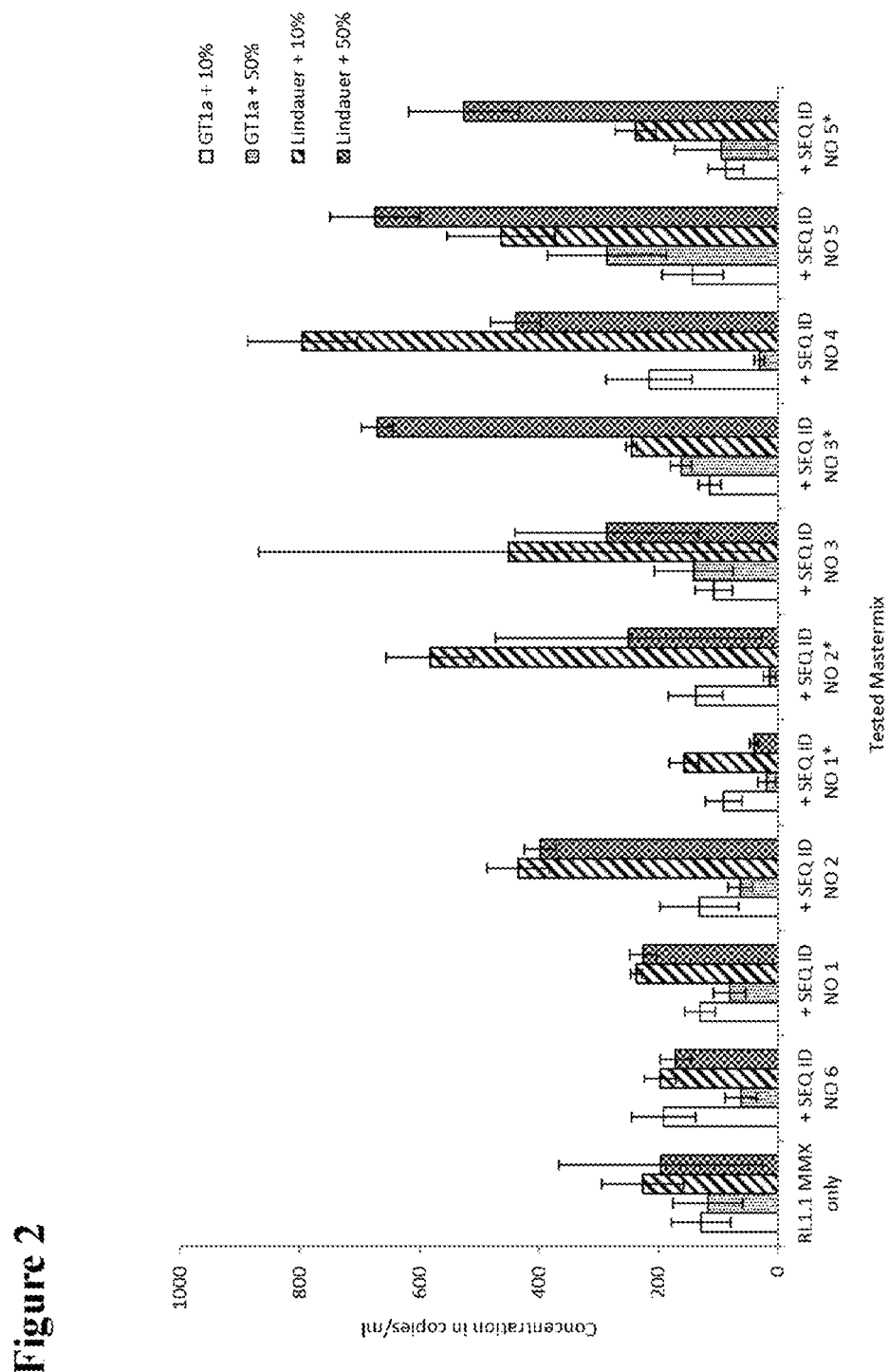

FIG. 2: Assessment of probes SEQ ID NOs: 1 to 5 using HCV RNA transcripts for HCV genotype 1a and for a naturally occurring mutant isolate (Lindauer).

Figure 3A:
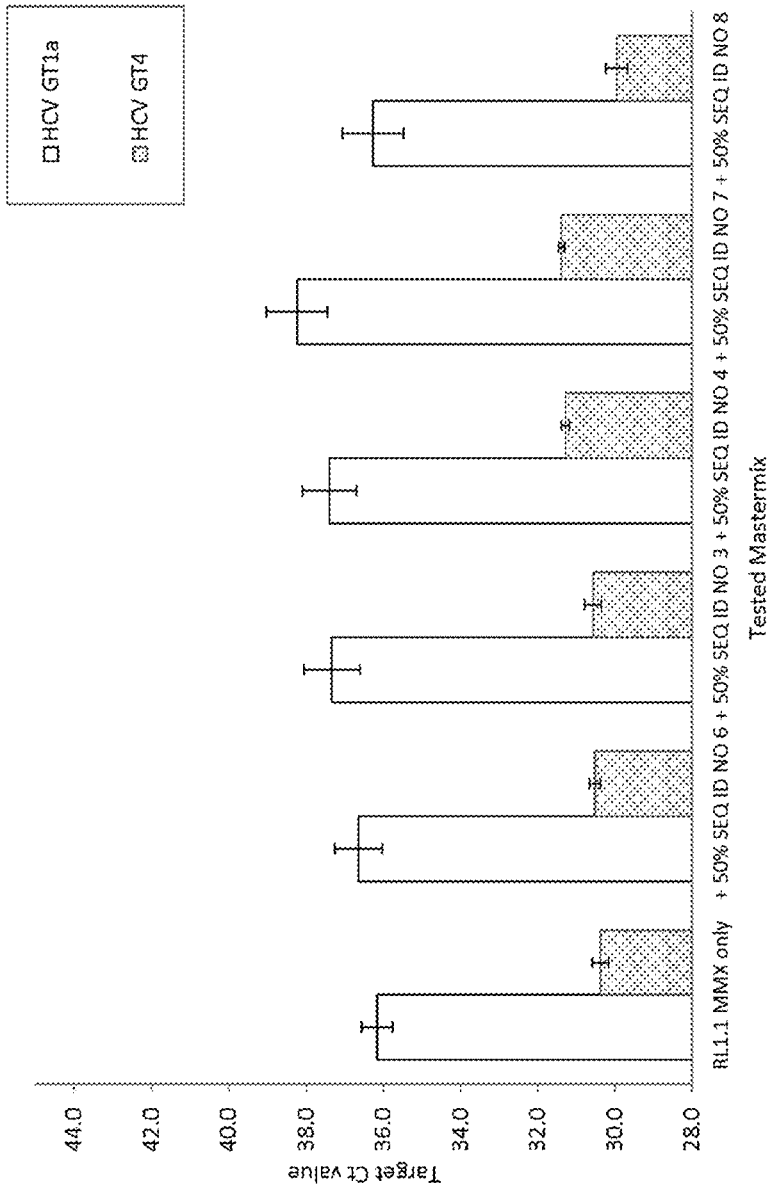
Figure 3B:
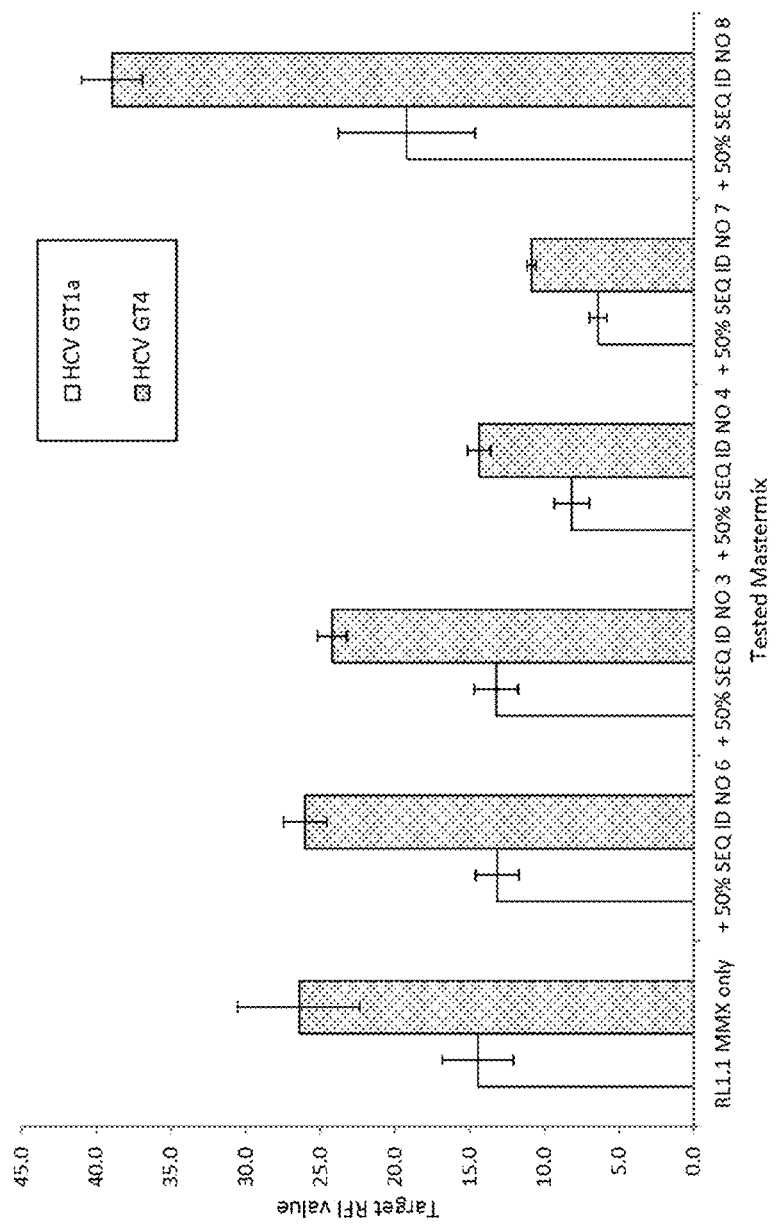

FIG. 3a-b: Assessment of non-overlapping probes SEQ ID NOs: 3, 4, 7 and 8 using HCV genotype 1a and 4a plasma samples. FIG. 3a: assessment of target ct values for an HCV GT1a and an HCV GT4a plasma sample. FIG. 3b: assessment of the fluorescence signal at the last PCR cycle for an HCV GT1a and an HCV GT4a plasma sample.

Figure 4A:
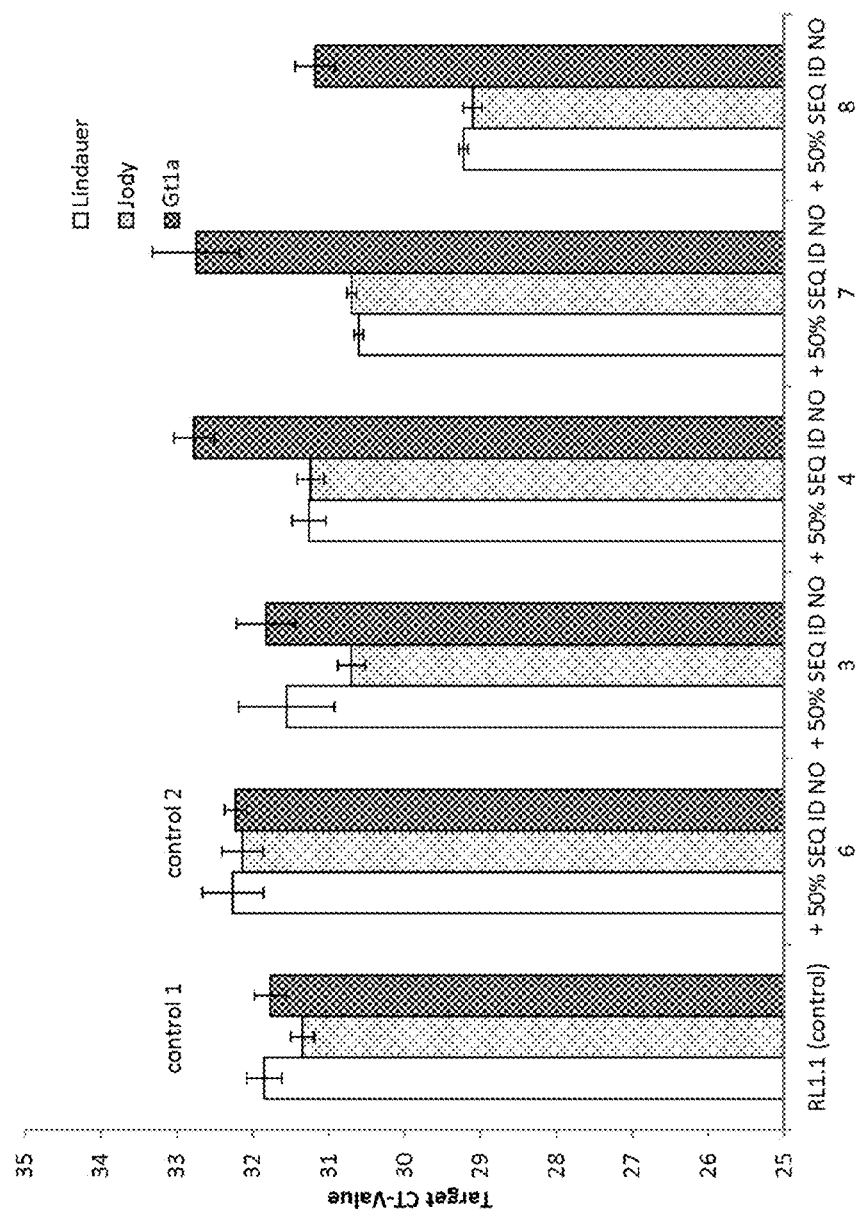

FIG. 4a-b: Assessment of non-overlapping probes SEQ ID NOs: 3, 4, 7 and 8 using transcript RNA for HCV genotype 1a (consensus) and for two naturally occurring mutant isolates (Jody, Lindauer). FIG. 4a: assessment of target ct values for three HCV RNA transcripts. FIG. 4b: assessment of fluorescence signal at the last PCR cycle for three HCV RNA transcripts.

Figure 5:
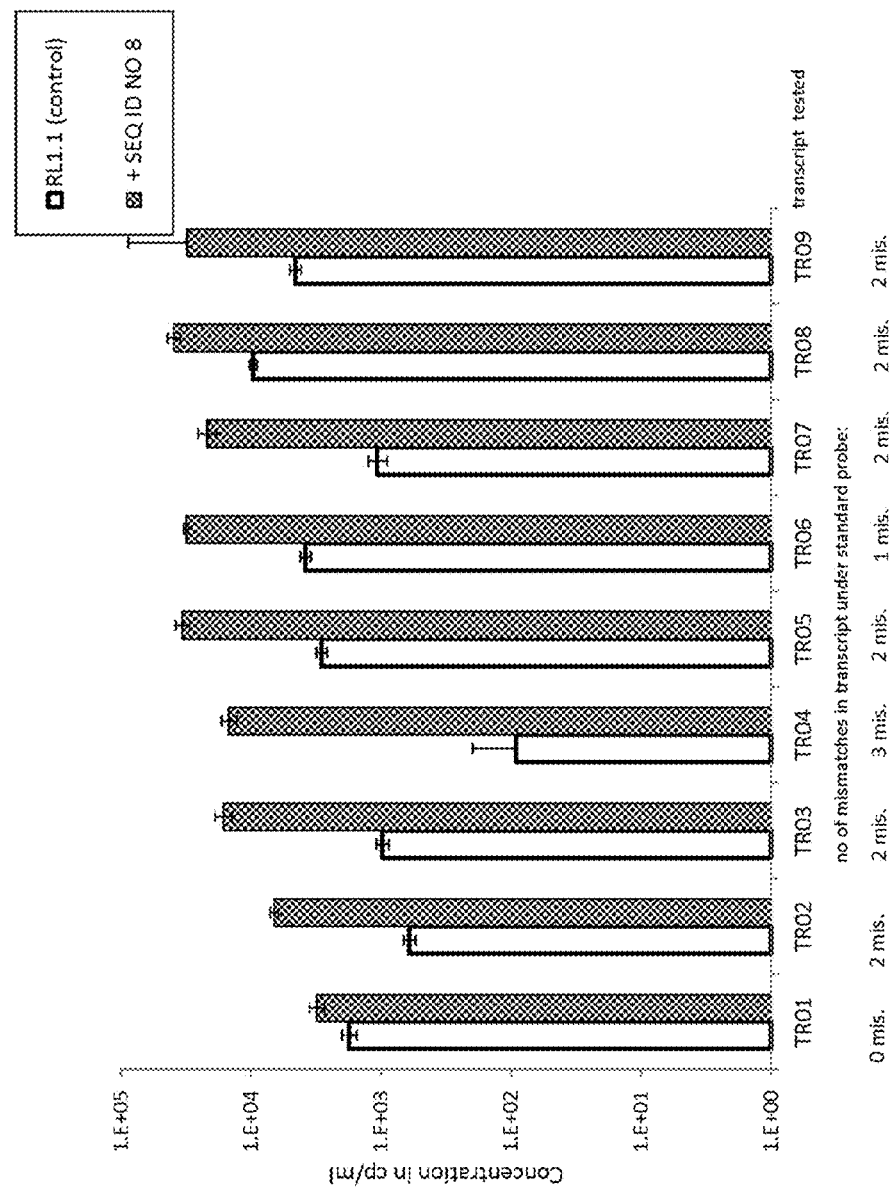

FIG. 5: Final assessment of probe SEQ ID NO:8 versus mastermix without second probe (RL1.1) using HCV RNA transcripts for HCV genotype 1a and for seven different naturally occurring mutant isolates.

Figure 6A:
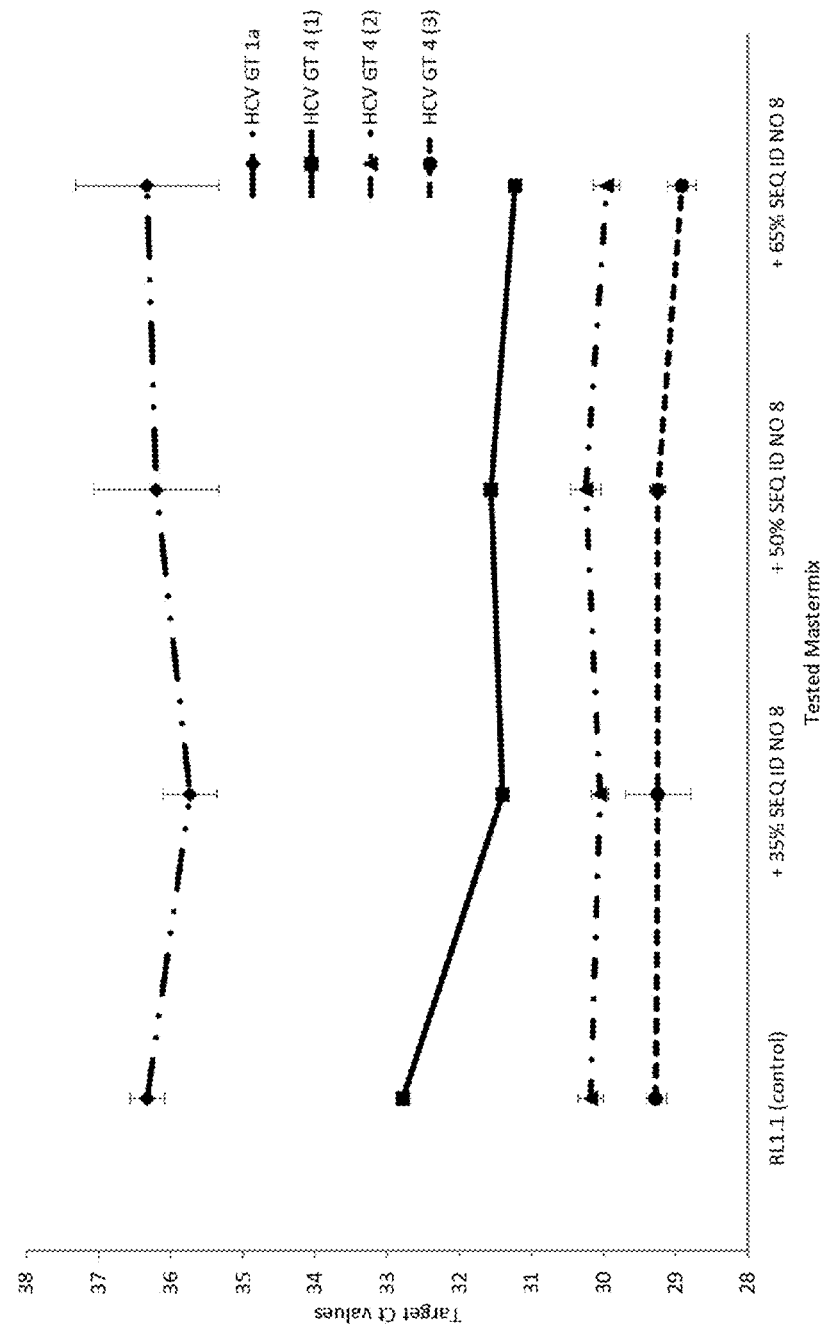
Figure 6B:
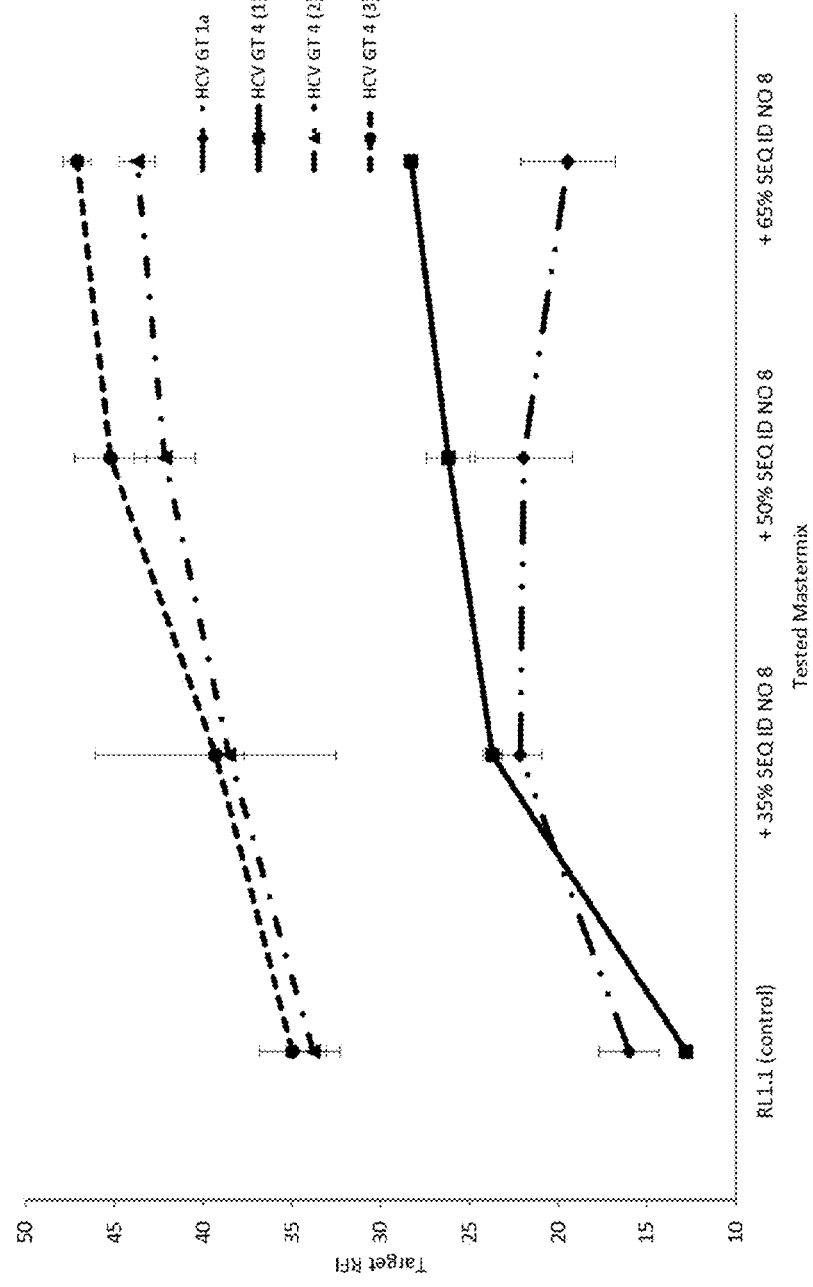

FIG. 6a-b: Concentration optimization for probe SEQ ID NO:8 (addition of 35%, 50% and 65%) versus reference mastermix RL1.1 using one patient HCV GT1a and three GT4a samples. FIG. 6a: assessment of target ct values for an HCV GT1a and three HCV GT4a plasma samples. FIG. 6b: assessment of the fluorescence signal at the last PCR cycle for an HCV GT1a and three HCV GT4a plasma samples.

DETAILED DESCRIPTION OF THE FIGURES

FIG. 1: schematic overview of probes tested to supplement original probe SEQ ID NO:6. Primers and probe with SEQ ID NOs: 6, 9, 10 and 11 belong to reference mastermix RL1.1 and are present in all experiments.

FIG. 2: assessment of titers (cp/mL) for two HCV RNA transcripts, a control transcript for HCV genotype 1a and a transcript with two naturally occurring mutations in the probe binding region of the amplicon (Lindauer) with mastermixes containing 10% additional or 50% additional second probe (relative to concentration of standard probe SEQ ID NO:6 in RL1.1). For the reference Mastermix RL1.1, bars 1 and 2 and bars 3 and 4 represent identical experiments as no additional probe is contained in the Mastermix. A second reference is RL1.1 with increased concentration of standard probe SEQ ID NO:6, 10% and 50%, but no second probe. Addition of SEQ ID NOs: 2, 3, 4, and 5 increases the concentration determined for the mismatch transcript. Note that SEQ ID NOs: 1 and 1*, 2 and 2*, 3 and 3* and 5 and 5*, respectively, are identical in sequence but contain different labels (see also FIG. 1).

FIG. 3a: assessment of target ct values for an HCV GT1a and an HCV GT4a plasma sample with mastermixes containing 50% additional second probe (relative to concentration of standard probe SEQ ID NO:6 in RL1.1). Reference Mastermix RL1.1 contains only one probe SEQ ID NO:6. A second reference is RL1.1 with 50% increased concentration of standard probe SEQ ID NO:6, but no second probe. Low target ct indicates early sample recognition; a delta of 3.3 Ct values indicates a 10-fold titer difference. Addition of probes SEQ ID NOs: 3, 4, and 7 slightly decrease performance in either GT1a and/or GT4a as the ct-values increase. Best performance is observed for SEQ ED NO:8.

FIG. 3b: assessment of the fluorescence signal at the last PCR cycle for an HCV GT1a and an HCV GT4a plasma sample with mastermixes containing 50% additional second probe (relative to concentration of standard probe SEQ ID NO:6 in RL1.1). Reference Mastermix RL1.1 contains only one probe, SEQ ID NO:6. A second reference is RL1.1 with 50% increased concentration of standard probe SEQ ID NO:6, but no second probe. High relative fluorescence index (RFI) indicates efficient amplification and signal generation. Addition of SEQ ID NOs: 4 and 7 decreases performance in GT1a and GT4a as the RFIs decrease. Best performance is observed for SEQ ID NO:8.

FIG. 4a: assessment of target ct values for three HCV RNA transcripts, a control transcript for HCV genotype 1a and 2 transcripts with naturally occurring mutations in the probe binding region of the amplicon with mastermixes containing 50% additional second probe (relative to concentration of standard probe SEQ ID NO:6 in RL1.1). Reference Mastermix RL1.1 contains only one probe, SEQ ID NO:6. A second reference is RL1.1 with 50% increased concentration of standard probe SEQ ID NO:6, but no second probe. Low target ct indicates early recognition of a sample; a difference of 3.3 Ct values indicates a 10-fold titer difference. Addition of SEQ ID NOs: 3, 4 and 7 show slight performance increase for the mutant transcripts as the ct-values decrease. Best performance is observed for SEQ ID NO. 8.

FIG. 4b: assessment of fluorescence signal at the last PCR cycle for three HCV RNA transcripts, a control transcript for HCV genotype 1a and two transcripts with naturally occurring mutations in the probe binding region of the amplicon with mastermixes containing 50% additional second probe (relative to concentration of standard probe SEQ ID NO:6 in RL1.1). Reference Mastermix RL1.1 contains only one probe, SEQ ID NO:6. A second reference is RL1.1 with 50% increased concentration of standard probe SEQ ID NO:6, but no second probe. High relative fluorescence index (RFI) indicates efficient amplification and signal generation. Addition of SEQ ID NOs: 3, 4 and 7 shows no improvement concerning RFI in the mutant transcripts. Clear improvement is observed for SEQ ID NO: 8.

FIG. 5: assessment of titers (cp/mL) for nine HCV RNA transcripts, a control transcript for HCV genotype 1a and transcripts with naturally occurring mutations in the probe binding region of the amplicon with mastermixes containing 50% additional second probe (relative to concentration of standard probe SEQ ID NO:6 in RL1.1). Reference Mastermix RL1.1 contains only one probe, SEQ ID NO:6. Addition of SEQ ID NO:8 increased the concentration for all mismatch transcripts (with mismatches under the standard probe) as compared to reference RL1.1 up to >100 fold.

FIG. 6a: assessment of target ct values for an HCV GT 1a and three HCV GT4a plasma samples with mastermixes containing 35%, 50% and 65% additional probe SEQ ID NO:8 (relative to concentration of standard probe SEQ ID NO:6 in RL1.1). Reference Mastermix RL1.1 contains only one probe, SEQ ID NO:6. Low target ct indicates early sample recognition; a delta of 3.3 Ct values indicates a 10-fold titer difference. All three concentrations of SEQ ID NO:8 performed similarly.

FIG. 6b: assessment of the fluorescence signal at the last PCR cycle for an HCV GT1a and three HCV GT4a plasma samples with mastermixes containing 35%, 50% and 65% additional probe SEQ ID NO:8 (relative to concentration of standard probe SEQ ID NO:6 in RL1.1). Reference Mastermix RL1.1 contains only one probe, SEQ ID NO:6. High relative fluorescence index (RFI) indicates efficient amplification and signal generation. Best results were obtained for addition of 50% of second probe SEQ ID NO:8.

EXAMPLES

General Experimental Design

All experiments were performed under equivalent experimental conditions. The basic master mix composition including the standard probe SEQ ID NO:6 was the same in all experiments and was designated mastermix RL1.1. RL1.1 was supplemented with additional 50% of either the original probe SEQ ID NO:6 or with one of the additional probes (SEQ ID NOs: 1-5, 7, or 8) for evaluation one at a time, according to the present invention. Each probe was added and assessed individually at the same concentration (10% or 50% of the original probe SEQ ID NO:6). The different second probes partly overlapped or did not overlap with the standard probe SEQ ID NO:6. Some of the probes were located on the same strand as the standard probe SEQ ID NO:6, some were located on the opposite strand.

In all experiments the mastermix RL1.1 without a second probe was tested as reference (control 1) as well as the mastermix with 10% or 50% increased concentration of the original probe SEQ ID NO:6 (control 2). The same sample preparation profiles, thermocycling profiles and result interpretation parameters were used for the assessment of the different mastermixes. As samples, either natural HCV GT1a and GT4a samples were used and tested in 10 replicates each or transcripts of the 5'untranslated region of HCV were tested in 4 to 6-fold replicates. Mean values across the replicates and standard deviation are presented in the graphs.

In initial experiments the probes SEQ ID NO 1-5 were assessed using HCV transcripts representing a standard GT1a and transcripts representing a mismatch isolate in the probe region. SEQ ID NOs: 2, 3, 4, and 5 showed the best initial performances. SEQ ID NOs: 3 and 4 were further evaluated together with additionally designed probes SEQ ID NOs: 7 and 8. SEQ ID NO:8 showed best performance in all experiments. A final evaluation using nine different transcripts representing a control transcript for HCV genotype 1a and transcripts with naturally occurring mutations in the probe binding region of the amplicon demonstrated that the addition of a second probe significantly increased the observed titer up to >100 fold for the transcripts carrying mismatches.

Example 1

Sample Material

HCV patient samples for HCV subtype 1a, representing the standard HCV samples, and HCV subtype 4a, representing HCV samples with possible sequence variation in the standard probe binding region, were tested to check the effect of adding a second probe to the mastermix. HCV RNA transcripts representing HCV GT1a consensus sequence and transcripts of the 5'untranslated region of naturally occurring HCV isolates in the amplicon region were used to evaluate the different second probes.

Nucleic Acid Extraction:

Per reaction 1 ml of patient plasma sample material was used for nucleic acid extraction. If transcripts were used, about 500 cp/ml (for experiments shown in FIGS. 2, 3a and 3b) or about 50 000 cp/ml (for experiments shown in FIGS. 4a, 4b and 5) were added to a guanidinium thiocyanate-containing buffer to inactivate RNases and 1 ml was then processed in the same way as a normal sample. A number of 5 to 10 replicates of the patient samples and 4 to 6 replicates of transcript samples were tested in each of the experiments.

Nucleic acid extraction methods are state-of-the-art and are known by the skilled artisan (see for example Sambrook et al., 2nd Edition 1989, Part 1-3, Molecular Cloning—A Laboratory Manual, Cold Spring Harbor Laboratory, Cold Spring Harbor, N.Y.; Oligonucleotide Synthesis (M. J. Gait, ed., 1984). Alternatively, commercially available nucleic acid extraction kits, i.e. the High Pure Viral Nucleic Acid Kit (Roche Diagnostics, Indianapolis, Ind., USA) or the Cobas® AmpliPrep Total Nucleic Acid Isolation Kit (TNAI) (Roche Diagnostics, Indianapolis, Ind., USA) can be used.

In the experiments described here the nucleic acid extraction was based on the Cobas® AmpliPrep Total Nucleic Acid Isolation Kit (TNAI) (Roche Diagnostics, Indianapolis, Ind., USA). The specimen preparation reagents consist of a magnetic glass particles suspension, a lysis reagent, a protease reagent, an elution buffer and a wash reagent. Quantitation Standard RNA was added to the specimens before nucleic acid extraction. The armored HCV particles and Quantitation Standard RNA armored particles are lysed by incubation with a protease and a chaotropic lysis/binding buffer that releases nucleic acids and protects the released HCV RNA from RNases in serum or plasma. Subsequently, the HCV RNA and Quantitation Standard RNA are bound to magnetic glass particles. Unbound substances such as salts, proteins and other cellular impurities are removed by washing the magnetic particles. The adsorbed nucleic acids are eluted at elevated temperature with an aqueous buffer.

PCR Reaction Mixture:

The master mixes evaluated consisted of the reference mastermix RL1.1 which was supplemented with the different probes. The reference mastermix RL1.1 was prepared in a large batch. For each experiment this master mix was supplemented with additional 10% or 50% of the standard probe SEQ ID NO:6 or with additional 10% or 50% of the individual second probes to be assessed as specified in the FIGS. 2-6.

Mastermix Composition RL1.1:

| Chemical | Concentration |
| --- | --- |
| Tricine | 157 mM |
| Potassium acetate | 314 mM |
| DMSO | 15.8% |
| Sodium Azide | 0.09% |
| Glycerol | 14.4% |
| Potassium Hydroxide | 36.9 mM |
| dNTPs (dATP, dCTP, dGTP, dUTP) | 1.29 mM each |
| Fwd primer SEQ ID NO 9 | 2.14 µM |
| Rev primer SEQ ID NO 10 | 1.07 µM |
| Rev primer SEQ ID NO 11 | 1.07 µM |
| Target probe SEQ ID NO: 6 | 428 nM |
| Second probe SEQ ID NOs: 1-5, 7 or 8* | 43 nM (10%) or 214 nM (50%) |
| QS Probe SEQ ID NO 16 | 428 nM |
| ZO5 polymerase | 2280 KU/L |
| UNG | 114 KU/L |
| Aptamer | 860 nM |
| pH | 7.8 |

*different second probe in each experiment; different concentrations in experiments to obtain data of FIG. 6.

Aptamers are short, single-stranded DNA- or RNA-oligonucleotides (25-70 bases), which bind to a specific molecule (i.e. protein, thermostable DNA polymerase from *Thermus aquaticus*) through their 3D structure (see for example C. Tuerk and L. Gold: Systematic evolution of ligands by exponential enrichment: RNA ligands to bacteriophage T4 DNA polymerase, Science, volume 249, 1990, p. 505-510).

50 µL of nucleic acid containing eluate were added to 35 µL of master mix and 15 µl, of 18 mM manganese acetate in PCR tubes and loaded onto the Cobas® TaqMan®48 Analyzer.

PCR Reaction:

The following thermal cycling steps were applied:

| Duration | Temperature | Repetitions |
| --- | --- | --- |
| 5 min | 50° C. | 1 |
| 30 min | 66° C. | 1 |
| 15 sec | 95° C. | 52 |
| 25 sec | 58° C. | 52 |
| 2 min | 40° C. | 1 |

Data Analysis:

The titers, ct-values or Relative fluorescence indices (RFI) across replicates of a sample, obtained as results from the Cobas® TaqMan® instrument, were averaged and the mean values with standard deviation were plotted as bar graphs as shown in FIGS. 2-5. The positive effect of a probe was assessed either by i) titer increase versus the reference master mix, or ii) decrease in ct value together with RFI increase versus the reference master mix.

Example 2

The experiments presented here can also be carried out as follows: The commercially available Cobas® AmpliPrep/Cobas® TaqMan® HCV Test (manufactured by Roche Molecular Systems, Pleasanton, Calif., USA) is used for extracting HCV RNA from the patient and the transcript samples. Specimen preparation is automated using the Cobas® AmpliPrep Instrument and amplification/detection is automated using the Cobas® TaqMan® Analyzer or the Cobas® TaqMan® 48 Analyzer. The test is based on three major processes: (1) specimen preparation to isolate RNA from human EDTA plasma or serum and controls which are provided in secondary tubes on the Cobas® AmpliPrep Instrument; (2) reverse transcription of the target RNA and the Quantitation Standard/Internal Control RNA to generate complementary DNA (cDNA) and (3) PCR amplification of target cDNA and Quantitation Standard/Internal Control cDNA with simultaneous detection of the generated amplicons on the Cobas® TaqMan® Analyzer by cleavage of dual-labeled detection probes specific to the target and to the Quantitation Standard/Internal Control.

The specimen preparation reagents consist of a magnetic glass particle suspension, a lysis reagent, a protease reagent, an elution buffer and a wash reagent. The HCV particles as well as the Quantitation Standard/Internal Control particles are lysed by incubation with a protease and a chaotropic lysis/binding buffer that releases nucleic acids and protects the released HCV RNA from RNases in serum or plasma. Subsequently, the HCV RNA and Quantitation Standard RNA are bound to magnetic glass particles. Unbound substances such as salts, proteins and other cellular impurities are removed by washing the magnetic particles. The adsorbed nucleic acids are eluted at elevated temperature with an aqueous buffer. The specimen or control eluate is added to the master mix and transferred to the Cobas® TaqMan® Analyzer or the Cobas® TaqMan® 48 Analyzer for amplification and detection.

For the experiments presented here, the Cobas® AmpliPrep/Cobas® TaqMan® HCV Test master mix is replaced by a mastermix according to the table shown below and in addition by adding different second probes according to the information given below. The reagent cassette with the modified mastermix is used on the Cobas® AmpliPrep instrument. The master mix contains primer and probe pairs specific for both HCV RNA and Quantitation Standard/Internal Control RNA. The primer binding sites are shared by the HCV target and the Quantitation Standard/Internal Control. Primers and target probes are located in a highly conserved part of the 5'-untranslated region of the HCV genome. The detection of HCV target and Quantitation Standard is performed using a target-specific and a Quantitation Standard-specific dual-labeled oligonucleotide probe which permits independent identification of HCV target amplicon and HCV Quantitation Standard amplicon. The HCV Quantitation Standard is automatically added to each specimen at a known copy number by the Cobas® AmpliPrep and is carried through the entire specimen preparation, reverse transcription, amplification and detection steps along with the HCV target. The Quantitation Standard must give a positive signal in HCV target negative and positive specimens in order to enable titer determination. In partly suppressed or inhibited reactions the Quantitation Standard is affected similarly as the target and thus allows correct titer determination. Finally, the Quantitation Standard monitors HCV target negative reactions for inhibitory effects but due to its rather high concentration monitoring is not stringent.

Mastermix Composition RL1.1:

| Chemical | Concentration |
| --- | --- |
| Tricine | 157 mM |
| Potassium acetate | 314 mM |
| DMSO | 15.8% |
| Sodium Azide | 0.09% |
| Glycerol | 14.4% |
| Potassium Hydroxide | 36.9 mM |
| dNTPs (dATP, dCTP, dGTP, dUTP) | 1.29 mM each |
| Fwd primer SEQ ID NO 9 | 2.14 µM |

-continued

| Chemical | Concentration |
| --- | --- |
| Rev primer SEQ ID NO 10 | 1.07 µM |
| Rev primer SEQ ID NO 11 | 1.07 µM |
| Target probe SEQ ID NO: 6 | 428 nM |
| Second probe SEQ ID NOs: 1-5, 7 or 8* | 43 nM (10%) or 214 nM (50%) |
| QS Probe SEQ ID NO 16 | 428 nM |
| Z05 polymerase | 2280 KU/L |
| UNG | 114 KU/L |
| Aptamer | 860 nM |
| pH | 7.8 |

*different second probe in each experiment; different concentrations in experiments to obtain data of FIG. 6.

Aptamers are short, single stranded DNA- or RNA-oligonucleotides (25-70 bases), which bind to a specific molecule (i.e. protein, Z05) through their 3D structure (see for example C. Tuerk and L. Gold: Systematic evolution of ligands by exponential enrichment: RNA ligands to bacteriophage T4 DNA polymerase, Science, volume 249, 1990, p. 505-510).

The reference master mix RL1.1 without a second probe is prepared in a large batch. For each experiment this reference master mix is supplemented with the additional probes as shown in the Figures. These supplemented mastermix variations are filled into reagent cassettes and are loaded onto the Cobas® AmpliPrep instrument.

Data Analysis:

The titers, ct-values or Relative fluorescence indices (RFI) across replicates of a sample, obtained as results from the Cobas® TaqMan®, are averaged and the mean values with standard deviation are plotted as bar graphs as shown in FIGS. 2-5. The positive effect of a probe is assessed either by i) titer increase versus the reference master mix, or ii) decrease in ct value together with RFI increase versus the reference master mix.

Result:
1. SEQ ID NO:8 overall achieved the best results. In an assessment using nine different transcripts, one reference transcript for GT1a and eight transcripts with mutations in the probe binding region of SEQ ID NO:6, a titer increase was observed for every mutant transcript, up to 100-fold. Probe SEQ ID NO:8 does not overlap with the standard probe SEQ ID NO:6 and is located on the opposite strand.
2. A concentration optimization experiment for addition of SEQ ID NO:8 showed best results in teens of low ct values and high RFI values for an addition of 50% second probe relative to concentration of standard probe SEQ ID NO:6 in RL1.1.
3. SEQ ID NOs: 2, 3, 4, and 5 showed initial promising results. Increase in the titer of a mutant transcript can therefore be obtained by adding second probes which are partly overlapping, probes which are very close to the standard probe on the same strand or the opposite strand or non-overlapping probes on the same or the opposite strand:
    SEQ ID NO:2 overlaps with the standard probe SEQ ID NO:6 and is located on the opposite strand.
    SEQ ID NO:3 is located on the same strand as SEQ ID NO:6 with one base spacing with regard to the standard probe SEQ ID NO:6.
    SEQ ID NOs:4, 7 and 8 do not overlap with the standard probe SEQ ID NO:6 and are located on the opposite strand.
    SEQ ID NO:5 is analogous to the standard probe SEQ ID NO:6 but carries mutations which are not covered by SEQ ID NO:6.

It is understood that the examples and embodiments described herein are for illustrative purposes only and that various modifications or changes in light thereof will be suggested to persons skilled in the art.

The invention claimed is:

1. A method for amplifying and detecting a target nucleic acid of hepatitis C virus (HCV) that may be present in a sample, said target nucleic acid comprising subgroups with one or more sequence variations, said method comprising:
   (a) contacting nucleic acids from said sample with amplification reagents comprising a DNA polymerase, nucleotide monomers, primers effective for generating an amplicon from said target nucleic acid, and at least two detectable probes specific for different sequence portions of said amplicon, wherein the at least two detectable probes specific for different sequence portions of said amplicon carry the same label, wherein the at least two detectable probes hybridize to said amplicon in the same reaction vessel and under the same reaction conditions, wherein the primers are selected from the group consisting of SEQ ID NOs: 9-15, or complementary sequences thereof;
   (b) incubating said nucleic acids with said amplification reagents for a period of time and under conditions sufficient for an amplification reaction to occur; and
   (c) detecting the presence or absence of said amplicon by detecting hybridization of said at least two detectable probes to said different sequence portions of said amplicon, wherein said at least two detectable probes are SEQ ID NOS: 8 and 6, or complementary sequences thereof, and wherein the presence of said amplicon is indicative of the presence of said target nucleic acid comprising subgroups with one or more sequence variations in said sample.

2. The method of claim 1, wherein the at least two detectable probes do not overlap.

3. The method of claim 1, wherein said amplification reagents further comprise a control nucleic acid.

4. The method of claim 1, further comprising determining the quantity of the target nucleic acid comprising subgroups with one or more sequence variations after or during step (c).

5. The method of claim 1, wherein the at least two detectable probes specific for different sequence portions of said amplicon are 5'-nuclease probes.

6. The method of claim 1, wherein the at least two detectable probes specific for different sequence portions of said amplicon hybridize to the same strand of said amplicon.

7. The method of claim 1, wherein the at least two detectable probes specific for different sequence portions of said amplicon hybridize to different strands of said amplicon.

8. The method of claim 1, wherein the at least two detectable probes specific for different sequence portions of said amplicon hybridize to the amplicon at sites having no more than 100 bases between each other.

9. A method for amplifying and detecting a target nucleic acid of hepatitis C virus (HCV) that may be present in a sample, said target nucleic acid comprising subgroups with one or more sequence variations, said method comprising:
   (a) contacting nucleic acids from said sample with amplification reagents comprising a DNA polymerase, nucleotide monomers, primers effective for generating an amplicon from said target nucleic acid, and at least two detectable probes, wherein the at least two detectable probes hybridize to the amplicon in the same reaction vessel and under the same reaction conditions, wherein the at least two detectable probes comprise at least one pair of oligonucleotides in proximity to each other such that the emission spectrum of the donor fluorescent moiety overlaps with the absorption spectrum of the acceptor fluorescent moiety, and wherein fluorescence is detectable upon hybridization of the pair of oligonucleotides to the amplicon, wherein one oligonucleotide of the pair comprises an acceptor fluorescent moiety and the other oligonucleotide of the pair comprises an acceptor fluorescent moiety, wherein the primers are selected from the group consisting of SEQ ID NOs: 9-15, or complementary sequences thereof;

(b) incubating said nucleic acids with said amplification reagents for a period of time and under conditions sufficient for an amplification reaction to occur; and (c) detecting the presence or absence of said amplicon by detecting hybridization of the pair of oligonucleotides to said different sequence portions of said amplicon, wherein the pair of oligonucleotides are selected from the group consisting of SEQ ID NOS: 1-8, or complementary sequences thereof, and wherein the presence of said amplicon is indicative of the presence of said target nucleic acid comprising subgroups with one or more sequence variations in said sample.

* * * * *